(12) United States Patent
Veirman et al.

(10) Patent No.: US 9,297,774 B2
(45) Date of Patent: Mar. 29, 2016

(54) DETERMINATION OF THE INTERSTITIAL OXYGEN CONCENTRATION IN A SEMICONDUCTOR SAMPLE

(71) Applicant: COMMISSARIAT A L'ENERGIE ATOMIQUE ET AUX ENERGIES ALTERNATIVES, Paris (FR)

(72) Inventors: Jordi Veirman, Poisy (FR); Sébastien Dubois, Scionzier (FR); Nicolas Enjalbert, Burlats (FR)

(73) Assignee: COMMISSARIAT À L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 3 days.

(21) Appl. No.: 14/390,985

(22) PCT Filed: Apr. 5, 2013

(86) PCT No.: PCT/FR2013/000090
§ 371 (c)(1),
(2) Date: Oct. 6, 2014

(87) PCT Pub. No.: WO2013/150194
PCT Pub. Date: Oct. 10, 2013

(65) Prior Publication Data
US 2015/0055677 A1    Feb. 26, 2015

(30) Foreign Application Priority Data

Apr. 6, 2012  (FR) ...................................... 12 01045

(51) Int. Cl.
G01N 27/04    (2006.01)
H01L 21/66    (2006.01)
(Continued)

(52) U.S. Cl.
CPC ............ *G01N 27/041* (2013.01); *G01N 27/125* (2013.01); *H01L 22/12* (2013.01); *H01L 22/14* (2013.01); *G01N 2033/0095* (2013.01)

(58) Field of Classification Search
CPC ..... G01N 27/041; G01N 27/04; G01N 27/14; G01N 27/02; H01L 22/12; H01L 22/14
USPC ........................ 73/866; 324/451, 719; 374/45
See application file for complete search history.

(56) References Cited

U.S. PATENT DOCUMENTS 4,344,815 A * 8/1982 Cazarra .................. C30B 29/06
117/14
6,206,961 B1 * 3/2001 Takeno ............... H01L 21/3225
117/14

(Continued)

FOREIGN PATENT DOCUMENTS

FR          2 964 459        3/2012
JP          57-012356   *    6/1980

OTHER PUBLICATIONS

Ulyashin et al., "Characterization of the oxygen distribution in Czochralski silicon using hydrogen-enhanced thermal donor formation," *Materials Science & Engineering B*, 2000, pp. 124-129, vol. 73.

(Continued)

*Primary Examiner* — Peter Macchiarolo
*Assistant Examiner* — Nathaniel Kolb
(74) *Attorney, Agent, or Firm* — Oliff PLC

(57) ABSTRACT

A method for determining the oxygen concentration of a sample made from p-type semiconductor material includes a thermal treatment step to form the thermal donors, a measuring step of the charge carrier concentration of the sample at a temperature between 0 K and 100 K, a step of determining the thermal donor concentration of the sample from the charge carrier concentration and the temperature of the sample, and a step of determining the interstitial oxygen concentration from the thermal donor concentration.

11 Claims, 3 Drawing Sheets

(51) Int. Cl.
*G01N 27/12* (2006.01)
*G01N 33/00* (2006.01)

(56) References Cited

U.S. PATENT DOCUMENTS 8,571,812 B2 10/2013 Veirman et al.
2013/0158889 A1 6/2013 Veirman et al.

OTHER PUBLICATIONS

Simoen et al., "Characterisation of oxygen and oxygen-related defects in highly- and lowly-doped silicon," *Materials Science & Engineering B*, 2003, pp. 207-212, vol. 102.

Sassella et al., "Influence of oxygen precipitation on the measure of interstitial oxygen concentration in silicon from 1207 cm$^{-1}$ infrared absorption band," *Journal of Applied Physics*, Jan. 1, 2002, pp. 166-170, vol. 91, No. 1.

Saito et al., "Determination of Interstitial Oxygen Concentration in Oxygen-Precipitated Silicon Wafers by Low-Temperature High-Resolution Infrared Spectroscopy," *Jpn. J. Appl. Phys.*, Sep. 1, 1995, pp. L 1097-L 1099, vol. 34, Pt. 2, No. 9A.

Sze, *Physics of Semiconductor Devices*, 1981, pp. 16-21, Wiley-Interscience, New York.

Wijaranakula, "Formation kinetics of oxygen thermal donors in silicon," *Appl. Phys. Lett.*, Sep. 23, 1991, pp. 1608-1610, vol. 59, No. 13.

Londos et al, "Effect of Oxygen concentration on the kinetics of thermal donor formation in silicon at temperatures between 350 and 500 °C," *Appl. Phys. Lett.*, Mar. 29, 1993, pp. 1525-1526, vol. 62, No. 13.

\* cited by examiner

DETERMINATION OF THE INTERSTITIAL OXYGEN CONCENTRATION IN A SEMICONDUCTOR SAMPLE

BACKGROUND OF THE INVENTION

The invention relates to a method whereby the interstitial oxygen concentration of a p-type semiconductor sample is able to be determined.

STATE OF THE ART

Silicon substrates intended for the microelectronics industry or for photovoltaic applications comprise oxygen. When they are not in the form of precipitates, the oxygen atoms generally occupy interstitial positions in the crystal lattice. In the case of monocrystalline silicon obtained by the Czochralski process, or in the case of polycrystalline silicon of quality called "solar quality", the interstitial oxygen concentration $C_O$ varies between $10^{17}$ and $2*10^{18}$ atoms/cm$^3$.

The oxygen in interstitial position ($O_i$) plays an important role on the mechanical and electrical properties of silicon. In particular, at temperatures comprised between 200° C. and 500° C., the oxygen forms agglomerates called Thermal Double Donors (TDD) which modify the electrical properties of the material. At higher temperature, the oxygen forms precipitates enabling metallic impurities present in the silicon to be trapped. A getter effect can thus be obtained. Furthermore, oxygen improves the mechanical properties of the substrates by blocking the dislocations introduced by the fabrication methods.

For photovoltaic applications, a high oxygen concentration results in a reduction of performances under lighting, in particular a reduction of the conversion efficiency of p-doped silicon photovoltaic cells (the majority carriers of which are holes). In particular, this is the case of cells made from silicon doped with boron (B).

It therefore appears important to know the concentration and distribution of the interstitial oxygen in a p-type substrate to locally determine the influence of the oxygen on the electrical and mechanical properties of the silicon. This information then enables the crystallization or fabrication methods of the devices to be optimized.

The oxygen concentration of a semiconductor sample is conventionally determined by Fourier Transform InfraRed (FTIR) spectroscopy. However, this technique is slow and imprecise. It further requires a sample with a thickness of at least 200 μm and preparation of the surface of the sample.

Furthermore, FTIR spectroscopy does not enable concentrations $C_O$ of less than $10^{16}$ cm$^{-3}$ to be measured precisely. This limit concentration is moreover even higher in a highly doped silicon where the net doping $N_A-N_D$ is typically more than $5*10^{16}$ cm$^{-3}$. Absorption by the numerous charge carriers does in fact disturb measurement.

The article "Characterization of the oxygen distribution in Czochralski silicon using hydrogen-enhanced thermal donor formation" (A. G. Ulyashin et al., Materials Science and Engineering B73, 124-129, 2000) describes another technique for determining the oxygen concentration.

This technique is based on the formation of thermal double donors TDD. A hydrogen plasma-enhanced thermal treatment is applied to a sample of p-type silicon so as to form a p-n junction. The depth of the p-n junction in the sample is then determined by means of Spreading Resistance Probe (SRP) or Capacitance-Voltage (C-V) measurements. The thermal donor concentration is then calculated from the depth of the p-n junction. A mathematical model enables the oxygen concentration to be determined from the thermal donor concentration.

The characterization methods used require preparation of the sample, in the same way as FTIR. SRP characterization requires the sample to be bevelled to establish the resistance profile on the depth of the sample. C-V characterization uses metallic contacts at the surface of the sample. These contacts are difficult to remove without impairing or polluting the material of the sample.

Due to the complexity of these characterization methods, the technique of the above-mentioned article is slow and is difficultly applicable to microelectronics and photovoltaic industry substrates. In addition, the preparation and hydrogenation of the substrate make the latter unusable on completion of the measurement.

Furthermore, this technique does not apply to highly doped substrates. For these substrates, the quantity of thermal donors formed is not sufficient to make the p-n junction necessary for measurement appear.

The article "Characterisation of oxygen and oxygen-related defects in highly- and lowly-doped silicon" (E. Simoen et al., Materials Science and Engineering B102, 207-212, 2003) describes the same techniques for studying oxygen and oxygen precipitates in lowly-doped to highly-doped silicon. In particular, FTIR spectroscopy, at low temperature, enables the interstitial oxygen concentration in a highly doped p-type silicon to be measured. The SRP and C-V characterisation highlights the presence of thermal donors in oxygen-doped high-resistivity silicon having been subjected to thermal annealing at 450° C.

Patent application FR2964459 describes a technique for mapping the oxygen concentration of a silicon substrate. This technique is also based on the formation of thermal double donors in the silicon. A resistivity measurement is made before and after activation annealing of the thermal donors. The thermal donor concentration is then calculated from the resistivity values and from the mathematical model expressing the charge carrier mobility in the silicon. The interstitial oxygen concentration can then be obtained from the thermal donor concentration.

This technique shows good results for lowly-doped crystalline silicon samples (net doping $<5*10^{16}$ cm$^{-3}$), in particular n-type. When the p-type silicon samples are highly doped on the other hand (net doping $\leq 5*10^{16}$ cm$^{-3}$), generation of thermal donors does not lead to a sufficient resistivity variation to determine the interstitial oxygen concentration.

SUMMARY OF THE INVENTION

It is observed that a requirement exists to provide a method enabling the interstitial oxygen concentration to be determined in any type of p-type semiconductor sample.

This requirement tends to be met by the following steps:
  subjecting the sample to thermal treatment to form thermal donors;
  bringing the sample to a temperature comprised between 0 K and 100 K and measuring the charge carrier concentration of the sample;
  determining the thermal donor concentration of the sample from the charge carrier concentration and the temperature of the sample; and
  determining the interstitial oxygen concentration from the thermal donor concentration.

BRIEF DESCRIPTION OF THE DRAWINGS

Other advantages and features will become more clearly apparent from the following description of particular embodiments of the invention given for non-restrictive example purposes only and illustrated by means of the appended drawings, in which.

DESCRIPTION OF A PREFERRED EMBODIMENT OF THE INVENTION

Figure 1:
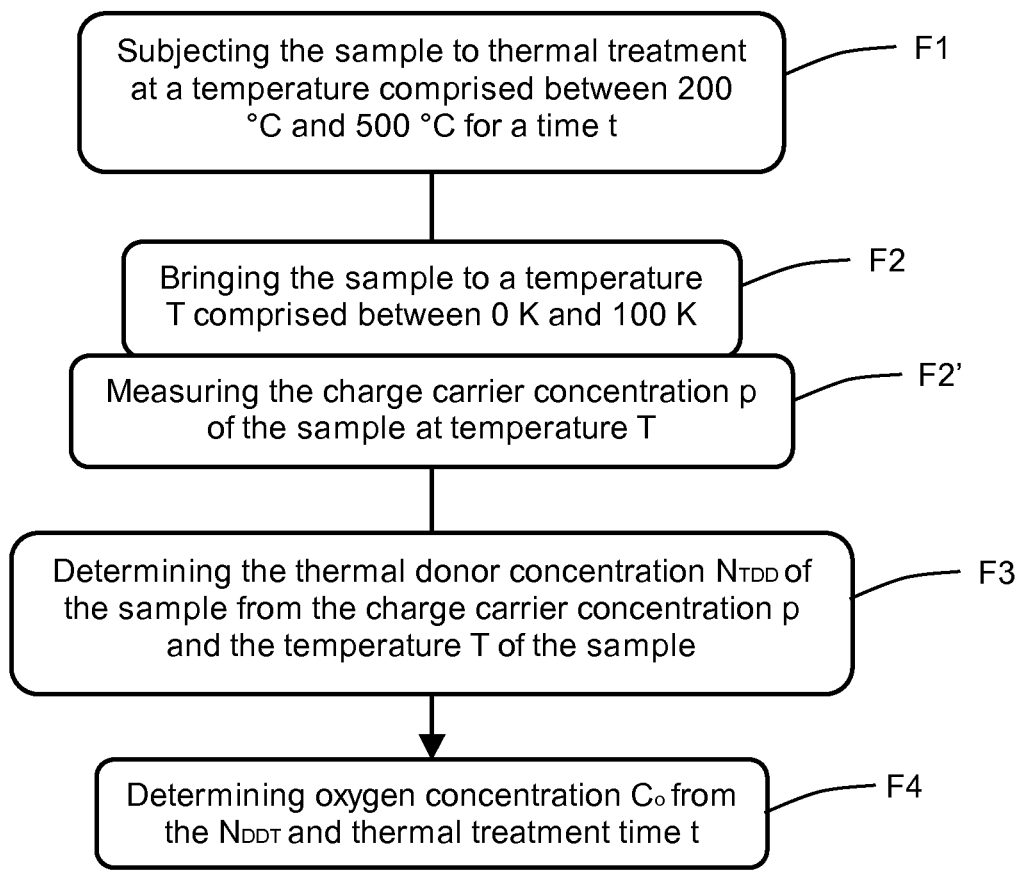
FIG. 1 represents steps of a method for determining the interstitial oxygen concentration $C_O$ according to the invention.

In a p-doped silicon substrate, the majority charge carriers are holes. At ambient temperature, their concentration is defined by the concentration of dopant impurities $N_A$ present in the silicon, generally boron atoms (B). These atoms are called electron acceptors.

On the contrary, in an n-type silicon, the majority charge carriers are electrons. The dopant impurities are electron donor atoms, for example phosphorus atoms (P). At ambient temperature, the electron concentration is given by the donor atom concentration $N_D$.

Substrates in addition exist called "compensated substrates" which present both types of dopant impurities, acceptors and donors (in concentration $N_A$ and $N_D$ respectively). The silicon is then p-type if $N_A$ is greater than $N_D$, and the hole concentration is equal to $N_A-N_D$ (at ambient temperature). On the contrary, the silicon is n-type if $N_D>N_A$, and the electron concentration is equal to $N_D-N_A$ (at ambient temperature).

By subjecting the silicon substrate to a temperature comprised between 200° C. and 500° C., thermal donors are formed in the substrate. The thermal donors TDD are considered as dopant impurities of "double" donor type, as each TDD generates two electrons.

Activation of the thermal donors TDD then causes a variation of the free charge carrier concentration in the substrate. If the latter is of n type, the electron concentration is increased by twice the thermal donor concentration $N_{TDD}$. In a p-type substrate on the other hand, the hole concentration is reduced by twice the concentration $N_{TDD}$, following rebalancing of the charges.

Only p-type semiconductors, and for example purposes silicon, considered in the following.

In a highly-doped silicon, the free charge carrier concentration, hereafter noted p, is high at ambient temperature ($p=N_A-N_D\geq 5*10^{16}$ cm$^{-3}$). Thus, when the variation of the concentration p caused by activation of the thermal donors TDD is to be measured, it is observed that this variation is small compared with the initial charge carrier concentration, about 4 to 5 decades.

It is then very difficult to measure this variation. In similar manner, when the silicon contains a low interstitial oxygen content, the activated thermal donors TDD are small in number. The charge carrier concentration p is then practically not modified when annealing is performed.

On the other hand, when this variation is observed at low temperature, between 0 K and 100 K, it is observed that the contribution of the thermal donors on the charge carrier concentration p is significant. This comes from the fact that at low temperature, the number of free charge carriers is considerably reduced and becomes of the same order of magnitude as the number of thermal donors TDD.

It is proposed here to put this observation into application to determine the interstitial oxygen concentration in precise manner in any type of p-type semiconductor material, in particular in a material that is highly doped and/or contains little oxygen (in principle).

FIG. 1 represents steps F1 to F4 of a method for determining the interstitial oxygen concentration $C_o$.

In a first step F1, a sample containing oxygen, for example a silicon substrate, is subjected to thermal treatment, or annealing, to form thermal donors TDD. The annealing temperature is preferably comprised between 200° C. and 500° C., and advantageously between 400° C. and 500° C. In fact, as will be described further on, the formation kinetics of the thermal donors is well known in this temperature range, in particular at 450° C. The annealing time t is preferably comprised between 1 minute and 10 hours. This time is a function of the doping level and of the oxygen content of the material: the higher the oxygen content, the shorter the annealing time will be, and the higher the charge carrier density, the longer the time will be.

The sample is then brought, in F2, to a temperature T comprised between 0 K and 100 K, and preferably between 4 K and 20 K. The charge carrier concentration p of the sample is then measured at this temperature (step F2').

The lower the measurement temperature T, the higher the precision on the oxygen concentration $C_O$ will be. The 4-20 K range is preferred as it represents a good trade-off between precision and ease of implementation The temperatures of this range are in fact easily reachable, unlike lower temperatures which require more complex and expensive equipment.

Charge carrier concentration p is preferably measured by Hall effect. This technique is precise in the above-mentioned temperature range, while at the same time being simple to implement. However, other techniques could be envisaged, in particular that based on measurement of the capacitance versus the voltage (C-V).

Step F3 of the method of FIG. 1 consists in determining the thermal donor concentration $N_{TDD}$ of the silicon sample from the charge carrier concentration p and temperature T of the sample.

For this, a relation p(T) has been established linking the charge carrier concentration p to the thermal donor concentration $N_{TDD}$ in a silicon sample, versus the temperature T.

The relation p(T) is given below in the general case of a compensated silicon, i.e. comprising impurities of acceptor type in concentration $N_A$, and impurities of donor type in concentration $N_D$ (other than the TDD donors). Naturally, after the annealing of step F1, the silicon also comprises thermal double donors in concentration $N_{TDD}$.

The electroneutrality equation in this silicon is written:

$$p = N_A^i - N_D - 2 \cdot N_{TDD} \quad (1)$$

The factor 2 arises from the "double" donor nature of the TDD.

$N_A^i$ is the concentration of ionized acceptor type impurities. It depends on the concentration $N_A$ in the following manner (as all the impurities of acceptor type are not ionized at low temperature):

$$N_A^i = \frac{N_A}{1 + 4 \times \frac{p}{N_V \times e^{\frac{-E_{A_i}}{kT}}}}. \quad (2)$$

By replacing $N_A^i$ by its expression (2) in relation (i) and then simplifying, the following is obtained:

$$p^2 + p \times \left(\frac{N_V \times e^{\frac{-E_A}{kT}}}{4} + 2 \times N_{TDD} + N_D\right) +$$

$$(N_D + 2 \times N_{TDD} - N_A)\left(\frac{N_V \times e^{\frac{-E_A}{kT}}}{4}\right) = 0$$

The solution of this second degree equation is written:

$$p(T) = -\frac{1}{2}\left(2 \times N_{TDD} + N_D + \frac{N_V}{4} e^{\frac{-E_A}{kT}}\right) + \quad (3)$$

$$\frac{1}{2}\sqrt{\left(2 \times N_{TDD} + N_D + \frac{N_V}{4} e^{\frac{-E_A}{kT}}\right)^2 + (N_A - 2 \times N_{TDD} - N_D) \times N_V e^{\frac{-E_A}{kT}}}$$

where $N_A$ is the concentration of dopant impurities of acceptor type, $N_D$ the concentration of dopant impurities of donor type, $N_V$ the equivalent density of states in the valence band, $E_A$ the energy level of the acceptor states (calculated with respect to the top of the valence band), k the Boltzmann's constant and T the temperature.

The values of the parameters $N_V$, $E_A$ and k, and their possible variation with respect to the temperature T, are known from the work "Physics of Semiconductor Devices" (S. M. Sze, Wiley-Interscience, New York, 1981).

Thus, when the p-type silicon contains dopant impurities of acceptor type only ($N_D$=0), the relation p(T) is written:

$$p(T) = -\frac{1}{2}\left(2 \times N_{TDD} + \frac{N_V}{4} e^{\frac{-E_A}{kT}}\right) + \quad (4)$$

$$\frac{1}{2}\sqrt{\left(2 \times N_{TDD} + \frac{N_V}{4} e^{\frac{-E_A}{kT}}\right)^2 + (N_A - 2 \times N_{TDD}) \times N_V e^{\frac{-E_A}{kT}}}.$$

By means of the above relations (3) and (4), the thermal donor concentration $N_{TDD}$ can be easily calculated from the charge carrier concentration p measured at a given temperature T.

Determination of the concentration $N_{TDD}$ can also be performed by means of calibration curves.

Figure 2:
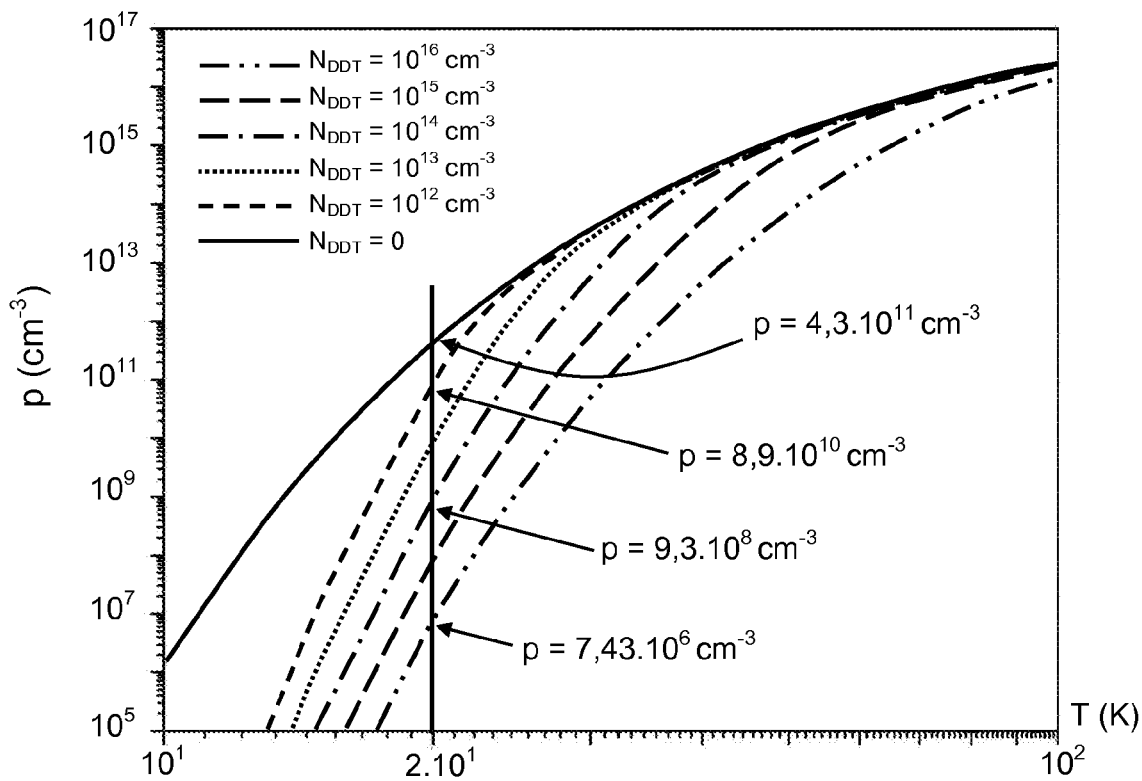
FIG. 2 represents a graph of the charge carrier concentration p in a highly-doped silicon sample versus the annealing temperature T for different values of the thermal donor concentration $N_{TDD}$.

FIG. 2 represents one of these calibration curves for example purposes. This one gives the charge carrier concentration p versus temperature T, for different values of $N_{TDD}$. It was established from relation (4) for a boron doped p-type silicon substrate ($N_A$=10$^{17}$ cm$^{-3}$).

For comparison purposes, the holes concentration p(T) for the same substrate, but devoid of thermal donors (bold plot), has also been represented on the calibration curve of FIG. 2.

It can be observed that formation of thermal donors TDD results in significant reductions of the holes concentration p. At 20 K for example, the concentration p is equal to 4.3*10$^{11}$ cm$^{-3}$ in the absence of thermal donors. It drops to 8.91*10$^{10}$ cm$^{-3}$ for a concentration $N_{TDD}$ equal to 10$^{12}$ cm$^{-3}$, to 9.3*10$^8$ cm$^{-3}$ for a concentration $N_{TDD}$ of 10$^{14}$ cm$^{-3}$ and to 7.43*10$^6$ cm$^{-3}$ for a concentration $N_{TDD}$ of 10$^{16}$ cm$^{-3}$. The concentration p therefore depends greatly on the concentration $N_{TDD}$ in the 0 K-100 K temperature range.

Reading of the calibration curve, for a given concentration p and temperature T, enables the thermal donor concentration $N_{TDD}$ to be obtained.

In step F4 (FIG. 1), the interstitial oxygen concentration $C_o$ of the sample is determined from the annealing time t and from the thermal donor concentration $N_{TDD}$ calculated in step F3.

The interstitial oxygen concentration $C_o$ is preferably calculated by means of a relation taken from the article "Formation kinetics of oxygen thermal donors in silicon" (Wijaranakula C. A. et al., Appl. Phys. Lett. 59 (13), pp. 1608, 1991). This article describes the formation kinetics of thermal donors in silicon by annealing at 450° C.

This temperature further constitutes a good trade-off between the rate of formation of the thermal donors and the maximum concentration obtained. A temperature greater than 450° C. enhances the rate of formation of the TDD to the detriment of the maximum concentration. A high temperature is therefore to be privileged when it is assumed that the oxygen concentration is high, for example greater than 5*10$^{17}$ cm$^{-3}$. On the contrary, a temperature lower than 450° C. will enable the maximum concentration of TDD to be increased and will be able to be used for substrates whose approximate oxygen concentration is low, for example less than 5*10$^{17}$ cm$^{-3}$.

Without prior information on the oxygen concentration, an annealing temperature comprised between 400° C. and 500° C., for example equal to 450° C., will preferably be chosen.

The relation expressing the thermal donor concentration $N_{TDD}$ versus the oxygen concentration $C_o$ and the annealing time t is given below:

$$N_{TDD}(t, C_o) = 4,51 \cdot 10^{-52} \times \left(C_o \left[1 + \frac{2}{3} D_o \times t \times C_o^{2/3}\right]^{-3/2}\right)^{3.45} \times t^{1.02}, \quad (5)$$

with $D_o$ the interstitial oxygen diffusion coefficient $$\left(D_o = 0.13 \times e^{\frac{2.53}{kT}}\right).$$

Knowing t and $N_{TDD}$, the interstitial oxygen concentration $C_o$ of the substrate can easily be calculated.

Alternatively, the interstitial oxygen concentration $C_o$ can be determined by means of calibration curves of the thermal donor concentration $N_{TDD}$ versus the annealing time t, for different values of the oxygen concentration $C_o$.

Figure 3:
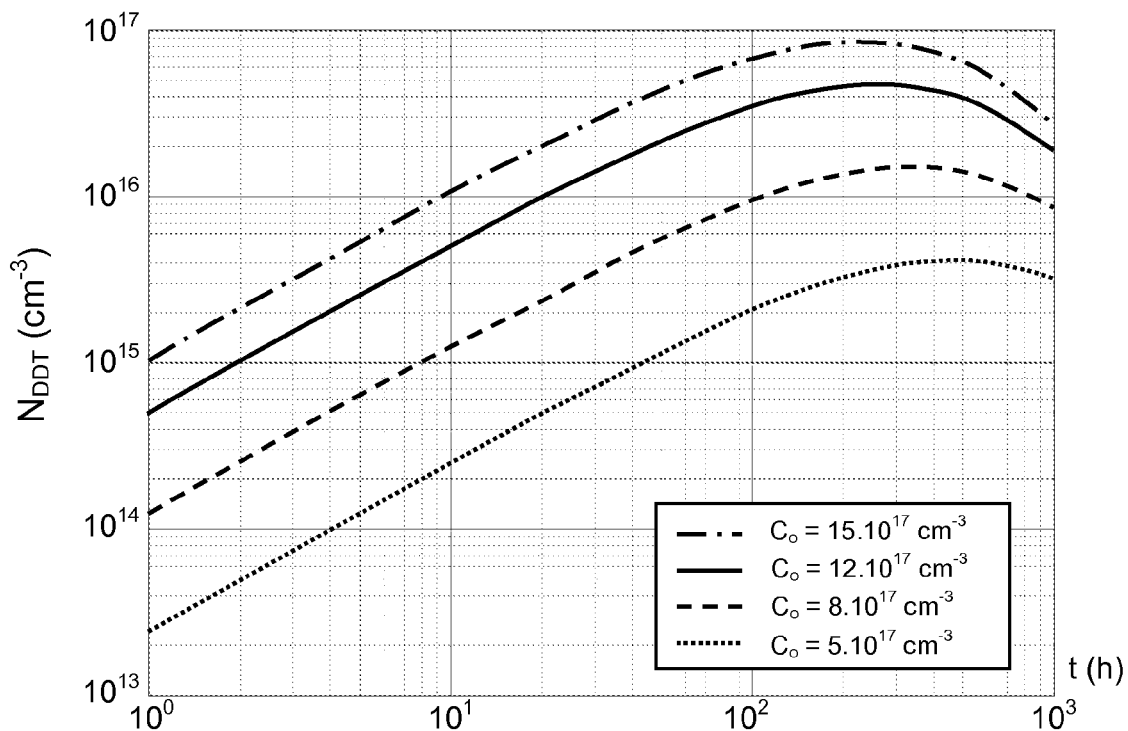
FIG. 3 represents a graph of the thermal donor concentration $N_{TDD}$ versus the thermal treatment time t for different values of the oxygen concentration $C_O$.

FIG. 3 represents one of these calibration curves built from relation (5) and for an annealing temperature of about 450° C. It can be observed that a small variation of the oxygen concentration $C_o$ results in a large variation of the thermal donor concentration $N_{TDD}$.

Reading of this calibration curve enables the value of the concentration $C_o$ to be determined for a given concentration $N_{TDD}$ and annealing time t.

For an annealing temperature different from 450° C., relation (5) and the calibration curves can be adapted, particularly in the light of the teachings of the article "Effect of oxygen concentration on the kinetics of thermal donor formation in silicon at temperatures between 350 and 500° C." (Londos C. A. et al., Appl. Phys. Lett. 62 (13), pp. 1525, 1993). This article also describes the formation kinetics of the thermal donors in the silicon, but for annealing temperatures comprised between 350° C. and 500° C.

Thus, by combining a measurement of p at low temperature and a mathematical model p(T) which takes account of the thermal donors, it is possible to determine the concentration $N_{TDD}$ precisely and to deduce the interstitial oxygen concentration therefrom.

For example purposes, if the concentration p is measured at 10 K, the detection limit of $C_O$ is lowered to $10^{16}$ cm$^{-3}$. In other words, it is possible to measure oxygen concentrations as low as $10^{15}$ cm$^{-3}$, which prior art techniques do not allow.

The calculation of $N_{TDD}$ performed in step F3 requires the value of the concentration of dopant impurities of acceptor type $N_A$, and possibly the concentration of dopant impurities of donor type $N_D$ (p-type compensated or not) to be known. These values can be given by the substrate manufacturer. If this is not the case, they can be determined in an additional step of the method of FIG. 1.

Figure 4:
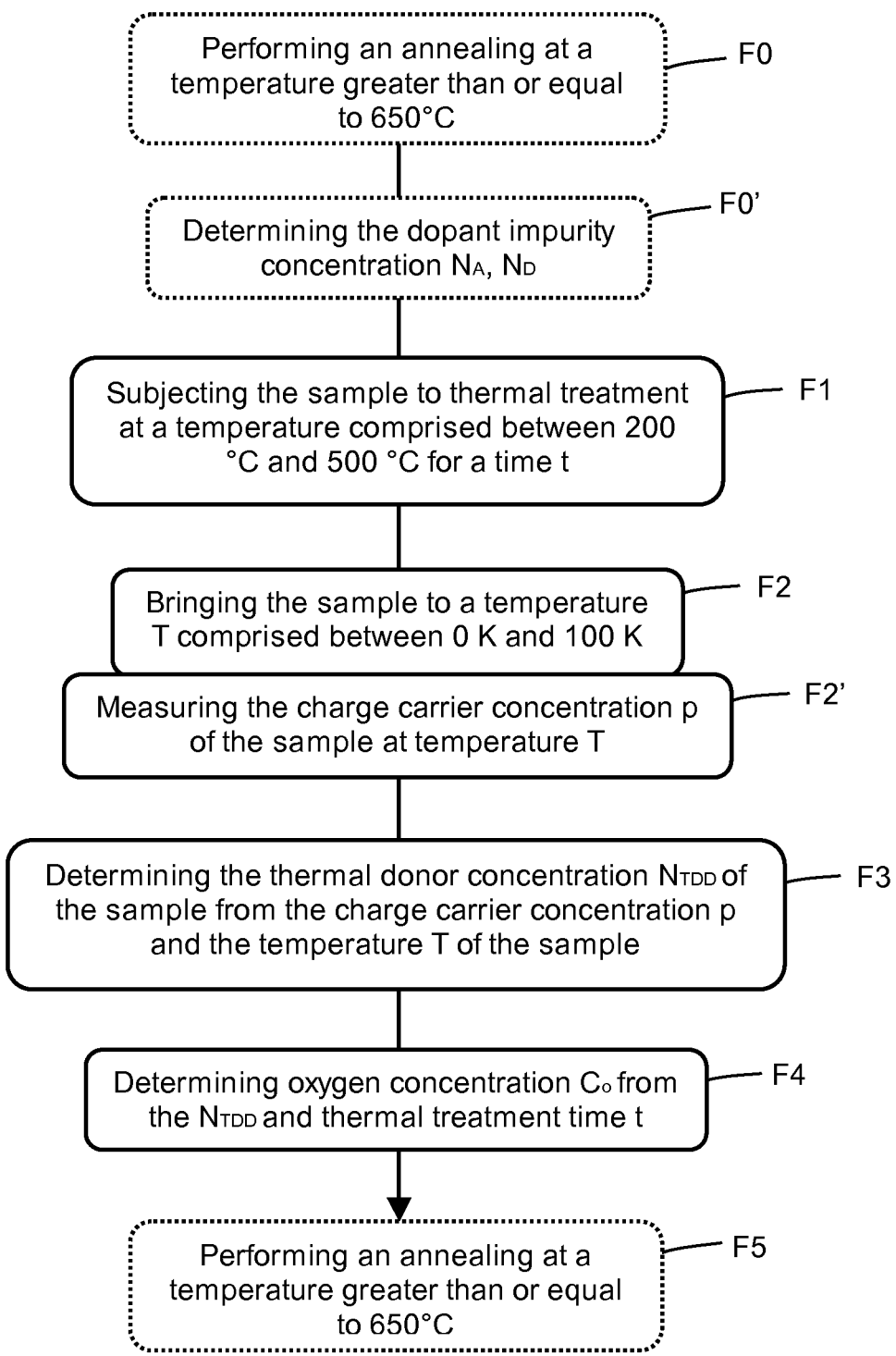
FIG. 4 represents additional steps of the method for determining the interstitial oxygen concentration $C_O$ of FIG. 1.

FIG. 4 represents additional steps of the method for determining, one of which enables the dopant impurity concentration $N_A$ or $N_D$ to be determined.

Preferably, the concentration $N_A$ or $N_D$ is determined in a step F0' prior to the annealing step F1.

For non-compensated p-type silicon (relation 4), the concentration $N_A$ can be calculated by means of the following relation, after the initial resistivity $\rho_o$ of the substrate has been measured:

$$\rho_0 = \frac{1}{N_A \cdot q \cdot \mu_p}, \quad (6)$$

q being the elementary charge (q=1.6*$10^{19}$ C) and $\mu_p$ the mobility of the holes in the silicon.

The resistivity measurement can be performed in simple manner by the four-point probes method or by a contact-free method, for example by inductive coupling.

In order to ensure that the substrate does not comprise any thermal donors in its initial state, which could result in a false value of $N_A$, annealing is preferably performed, in step F0, at a temperature greater than or equal to 650° C. This makes the oxygen precipitates (or thermal donors TDD) unstable and eliminates them. The oxygen atoms then resume their interstitial positions. Measurement of $\rho_o$ is therefore advantageously performed after such an annealing.

The annealing F0 can moreover be performed even when the concentration $N_A$ is known in order to ensure that the thermal donor concentration $N_{TDD}$ is initially zero. In other words, step F0 can be performed in the absence of step F0'.

Such an annealing is preferably also used at the end of the method, in F5, after the interstitial oxygen concentration has been determined (F4). By means of this annealing step F5, the substrate reverts to its initial state and can be reused.

In the case of compensated silicon (relation 3), it is necessary to know both the value of $N_A$ and the value of $N_D$. As previously, the initial resistivity of the substrate can be measured, provided that one of these two values is known.

If neither of them is known, additional measurements can be made, in particular measurement of GDMS (Glow Discharge Mass Spectroscopy) type.

In a preferred embodiment (not represented), the charge carrier concentration p is measured for different temperatures T comprised between 0 K and 100 K. Several pairs of values {p, T} are then obtained which can be correlated with relation (3) or (4) to determine the concentration $N_{TDD}$. It is then no longer even necessary to know the dopant impurity concentration $N_A$ in the case of relation (4). Knowing $N_D$ on the other hand remains necessary in the case of compensated silicon (relation 3).

Numerous variants and modifications of the method for determining described here will be apparent to the person skilled in the trade. The method has been described in relation with a silicon substrate. However, the method can also be applied to other p-doped semiconductors of group IV, in particular germanium or silicon-germanium substrates. Germanium is in fact also a semiconductor in which thermal donors can be formed in the presence of oxygen.

The invention claimed is:

1. A method for determining the interstitial oxygen concentration of a sample made from p-type semiconductor material from the thermal donor concentration, comprising the following step:

subjecting the sample to thermal treatment for a specified time to form thermal donors;

bringing the sample to a temperature comprised between 4 K and 100 K and measuring the charge carrier concentration of the sample;

determining the thermal donor concentration of the sample from the charge carrier concentration and the temperature of the sample; and determining the interstitial oxygen concentration from the thermal donor concentration and the specified time, as a function relating the thermal donor concentration, the interstitial oxygen concentration, and the specified time.

2. The method according to claim 1, comprising a plurality of measurements of the charge carrier concentration at different temperatures comprised between 4 K and 100 K, and wherein the thermal donor concentration is determined by correlation of the measurements with a relation describing the variation of the charge carrier concentration versus the temperature.

3. The method according to claim 2, wherein, the sample comprising dopant impurities of acceptor and donor type, the thermal donor concentration $N_{TDD}$ is determined by means of the following relation:

$$p(T) = -\frac{1}{2}\left(2 \times N_{TDD} + N_D + \frac{N_V}{4} e^{\frac{-E_A}{kT}}\right) + \frac{1}{2}\sqrt{\left(2 \times N_{TDD} + N_D + \frac{N_V}{4} e^{\frac{-E_A}{kT}}\right)^2 + (N_A - 2 \times N_{TDD} - N_D) \times N_V e^{\frac{-E_A}{kT}}}$$

wherein p(T) is the variation of the charge carrier concentration versus the temperature, $N_A$ is the concentration of dopant impurities of acceptor type, $N_D$ is the concentration of dopant impurities of donor type, $E_A$ the energy level of the acceptor states, $N_v$ the equivalent density of states in the valence band, k the Boltzmann's constant and T the temperature.

4. The method according to claim 3, comprising, before the thermal treatment step, a step of determining the dopant impurity concentration from a resistivity measurement of the sample.

5. The method according to claim 1, wherein, the sample comprising dopant impurities of acceptor and donor type, the thermal donor concentration $N_{TDD}$ is determined by means of the following relation:

$$p(T) = -\frac{1}{2}\left(2 \times N_{TDD} + N_D + \frac{N_V}{4}e^{\frac{-E_A}{kT}}\right) +$$

$$\frac{1}{2}\sqrt{\left(2 \times N_{TDD} + N_D + \frac{N_V}{4}e^{\frac{-E_A}{kT}}\right)^2 + (N_A - 2 \times N_{TDD} - N_D) \times N_V e^{\frac{-E_A}{kT}}}$$

wherein p(T) is the variation of the charge carrier concentration versus the temperature, $N_A$ is the concentration of dopant impurities of acceptor type, $N_D$ is the concentration of dopant impurities of donor type, $E_A$ the energy level of the acceptor states, $N_v$ the equivalent density of states in the valence band, k the Boltzmann's constant and T the temperature.

6. The method according to claim 5, comprising, before the thermal treatment step, a step of determining the dopant impurity concentration from a resistivity measurement of the sample.

7. The method according to claim 1, initially comprising an annealing step at a temperature greater than or equal to 650° C.

8. The method according to claim 1, wherein the charge carrier concentration is measured by Hall effect.

9. The method according to claim 1, wherein the thermal treatment is performed at a temperature comprised between 200° C. and 500° C.

10. The method according to claim 9, wherein the temperature of the thermal treatment is comprised between 400° C. and 500° C.

11. The method according to claim 1, wherein the sample is brought to a temperature comprised between 4 K and 20 K to measure the charge carrier concentration.

\* \* \* \* \*